United States Patent [19]

Gutnick

[11] 4,332,243

[45] Jun. 1, 1982

[54] DEVICES AND METHODS FOR THE PREVENTION OF TRANSMISSION OF VENEREAL DISEASE AND NON-GONOCOCCAL GENITAL INFECTIONS

[76] Inventor: Morton Gutnick, 8329 Fairview Rd., Elkins Park, Pa. 19117

[21] Appl. No.: 137,306

[22] Filed: Apr. 4, 1980

[51] Int. Cl.³ .............................................. A61F 13/00
[52] U.S. Cl. ............................................... 128/132 R
[58] Field of Search ................... 128/132 R, 271, 294, 128/260, 1 R

[56] References Cited

U.S. PATENT DOCUMENTS 2,410,460 11/1946 Robinson .............................. 128/294
2,904,041 9/1959 Brown .............................. 128/132 R
3,170,464 2/1965 Forti et al. .......................... 128/271

FOREIGN PATENT DOCUMENTS 133239 4/1901 Fed. Rep. of Germany ...... 128/271
859835 12/1940 France ................................. 128/294

Primary Examiner—John D. Yasko
Attorney, Agent, or Firm—Barnes, Kisselle, Raisch & Choate

[57] ABSTRACT

A method and devices for the prevention of transmission of venereal diseases and non-gonococcal genital infection which includes methods, such as contraceptive and non-contraceptive creams, jellies, foams, etc., and/or methods involving mechanical birth control devices such as condoms and cervical caps and vaginal diaphragms incorporating medication receptacles functioning to release medication in the form of contraceptive and non-contraceptive creams, jellies, foams, etc. by seepage or wall breaching during intercourse to expose the genital organs involved in intercourse to the medication and thus prevent the transmission of disease organisms.

8 Claims, 11 Drawing Figures

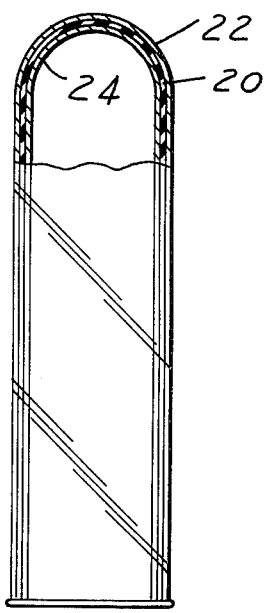
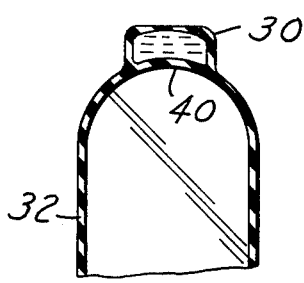
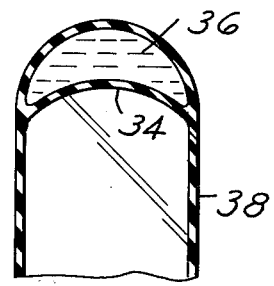
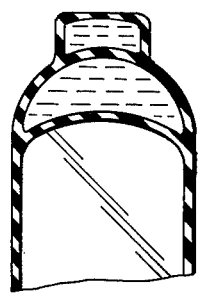
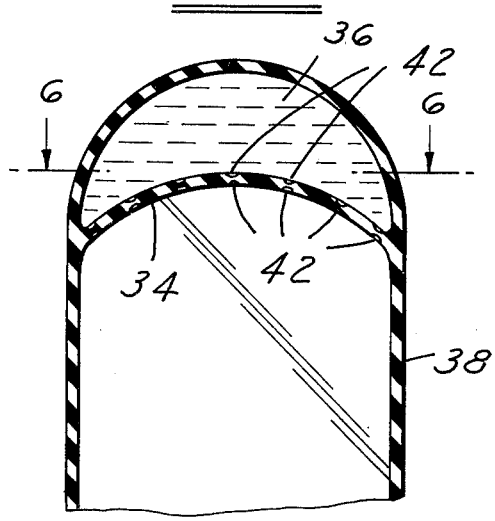
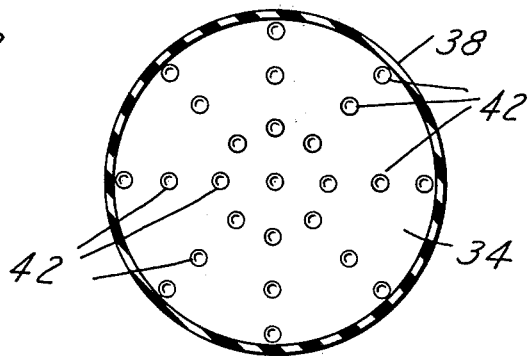

DEVICES AND METHODS FOR THE PREVENTION OF TRANSMISSION OF VENEREAL DISEASE AND NON-GONOCOCCAL GENITAL INFECTIONS

FIELD OF INVENTION

The method of, and devices for, the prevention of transmission of venereal disease utilizing contraception devices and associated medication.

BACKGROUND AND OBJECTS OF THE INVENTION

Attention is directed to my United States issued U.S. Pat. Nos. 3,913,573 (10/21/75) and 3,996,933 (12/14/76) on Intrauterine Contraceptive Devices and 4,102,998 (7/25/78) on a Process for Prevention of Venereal Disease. These patents are directed to intrauterine devices and are effective when utilized and properly inserted and maintained. However, many persons have not or will not seek medical aid for such protection and yet will utilize condoms, contraceptive sponges, diaphragms, vaginal suppositories, contraceptive and non-contraceptive liquids, creams, jellies and foams which can be self applied.

The incidence of venereal disease is increasing at an alarming rate as sexual morals change in the direction of more sexual promiscuity extending into younger and younger ages. Inasmuch as many persons engaged in sexual activity, whether within the accepted moral codes or without, are still concerned about birth control, a large number of partners in intercourse are willing to utilize mechanical birth control devices such as condoms and diaphragms, and/or contraceptive (and non-contraceptive) liquids, creams, salves, foams, etc.

It is, therefore, an object of the present invention to provide protection to both male and female partners whenever either one of them is willing to use birth control devices and methods of the type mentioned. This will increase the prevention coverage materially over those who seek medical aid in the form of intrauterine devices.

The invention contemplates the use of medicament chambers and medication layers which will provide protection against venereal disease and even some curative treatment in the event it is incipient or in the initial stages.

Other objects and features of the invention will be apparent in the following description and claims in which the invention is described and the manner and process of using the invention is set forth to enable a person skilled in the art to make and use the invention.

BRIEF DESCRIPTION OF THE INVENTION

The invention contemplates the application of medicament to the surfaces of mechanical birth control devices as well as special chambers which carry the desired medicament with a construction which effects release during intercourse to the vulnerable parts of the body.

BRIEF DESCRIPTION OF THE DRAWINGS

Drawings accompany the disclosure and the various views thereof may be briefly described as:

FIG. 1, a schematic view of a condom prepared in accordance with the invention.

FIG. 2, a modification showing a medicament chamber.

FIG. 3, a second modification showing a medicament chamber.

FIG. 4, an enlarged view of the modification of FIG. 3.

FIG. 5, another modification showing a double chamber.

FIG. 6, a sectional view on line 6—6 of FIG. 4.

DETAILED DESCRIPTION OF THE INVENTION AND THE MANNER AND PROCESS OF USING IT

Figure 7:
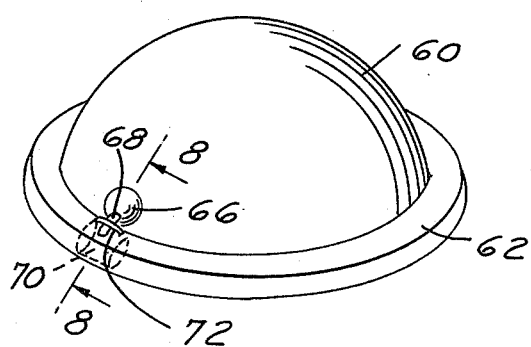
FIG. 7, a modification showing a diaphragm adapted to protective medicament dispensing.

With reference to the drawings, it must be appreciated that the present invention is intended to provide the following:

(1) The use of a minimum inhibitory concentration of medication (MIC) in vivo to prevent the transmittal of venereal disease;

(2) The ability to prevent non-gonococcal (such as chlamydia) genital infections and to intercept the organism of non-specific (or non-gonococcal) genital infection even in condom users, since the condom is permeable to these organisms;

(3) The availability of prophylaxes for both partners at the time of intercourse; and (4) Prevention, simultaneously, of venereal disease and pregnancy by the use of medication and a contraceptive device together with a spermicide at the time of contact during the act of intercourse, thus providing a method which does not require post-intercourse motivation.

Many medications are available to prevent venereal disease. It must be appreciated that in some geographical areas, the virulence of the gonococcus is much greater than others. The Taiwanese strain is about four times more virulent than that of the United States. The present invention allows the use of medication specific to various geographical areas.

Thus, the selection of the medication, and also the spermicide, if this is desired, can be made from available sources including antibiotics, antibacterials, Trichomonacides and Moniliacides. Contraceptive or non-contraceptive creams, jellies, salves, foams, and the like can be utilized as a medium for the release of the medication. Thus, the term anti-venereal medication can include any suitable available drug specific or general to cure and/or prevent venereal disease. An MIC dosage (minimum inhibitory concentration of the medication) can be used or prophylactic dosages as desired.

In FIG. 1, a diagrammatic presentation of a mechanical contraceptive device in the form of a prophylactic condom 20 is shown with an outside coating 22. This coating, which may partially or completely cover the condom, consists of a medium such as silicone oil or dry silicone containing an anti-venereal drug. A Silastic coating may also be used, the Silastic material being permeable and allowing the anti-venereal medication to diffuse outwardly. Silastic is a trademark used on a product of the Dow-Corning Corporation. It is a slippery, rubber-like material which has the property of leaching out drugs. No perforations in the material are required for this leaching out process. If the drug is admixed with the Silastic, while it is in the liquid state, it will leach out from the material. If the drug is placed in a Silastic pouch, the drug will diffuse through the wall of the pouch. The rate of diffusion can be varied in three ways: by making the Silastic membrane thinner or thicker, by varying the surface area, or by adding substances to the Silastic. Also, in FIG. 1, an inside coating 24 can be used. Similarly, a spermicide may be incorporated in the medication.

In use, the condom will release the medication so that both participants in the intercourse will be protected.

In FIGS. 2, 3, 4 and 5, condom constructions are shown with formed pouches to carry the medication.

FIG. 2 illustrates a pouch type appendage container 30 at the distal end of a condom 32 and FIG. 3 shows a liner septum wall 34 forming an end chamber 36 on a condom 38. A septum wall 40 in FIG. 2 and the septum wall 34 of FIG. 3 are formed with opposed indentations 42 to provide easily burstable breach areas which will release the medication inside the condom. See FIG. 6. In FIG. 5, a composite appendage 44 and a septum 46 are provided on a condom 48 to form chambers 50 and 52 carrying medication with the wall weaknesses being provided in the top wall 54 of chamber 50 and in the septum 46 of chamber 52 so that in the act of intercourse both chambers will be ruptured or breached to allow egress of the contents. Thus, protection will be provided for both the male and female organs for not only venereal disease but other non-gonococcal genital infections as well as for contraceptive purposes. The breach areas are such that many of them will rupture and cause a distribution of the medication circumferentially.

In FIGS. 7 to 11, a second type of mechanical contraceptive device in the form of a vaginal diaphragm or cervical cap is shown to accomplish the distribution of the medication.

Figure 8:
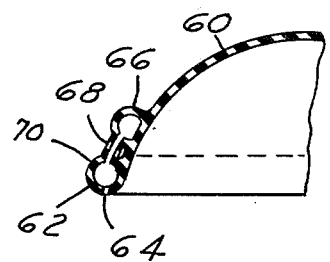
FIG. 8, a sectional view on line 8—8 of FIG. 7.

In FIG. 7, a contraceptive diaphragm 60 has an annular hollow rim 62. A small pouch or sac 66 contains a suitable medication in the form of an anti-venereal disease material and this sac is connected by a channel 68 (FIG. 8) to a Silastic container or pouch 70. The walls of the channel 68 are compressible so that a small clip 72 closes the channel when in position. Prior to using the diaphragm, the clip 72 is removed and the contents of the pouch 66 are squeezed into the Silastic pouch 70 and will start to diffuse outwardly. After removal of the diaphragm, the flow from pouch 70 to pouch 66 can be reversed and the clip 72 reapplied. A sectional view in FIG. 8 shows the structure and openings 74 can be provided in the rim 62 if desired to facilitate the distribution of the medication.

Figure 9:
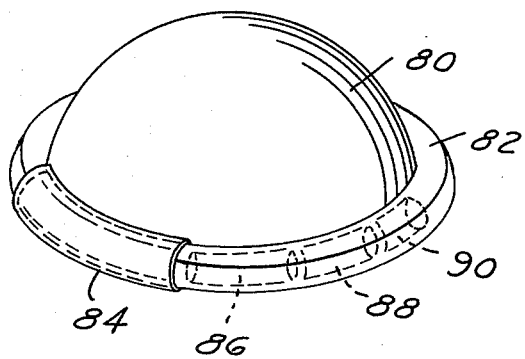
FIG. 9, a modification showing a diaphragm with several refillable chambers.

In FIG. 9, a diaphragm 80 is shown with a rim 82 which can carry a number of medicament supplies. An arcuate matrix 84, U-shaped in cross-section, is designed to snap on to the hollow rim 82 and impregnated with an anti-venereal drug. This drug will diffuse into the vagina over a period of time and the matrix can be replaced with a fresh unit from time to time.

Figure 10:
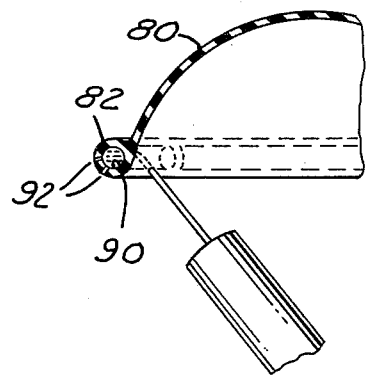
FIG. 10, an illustration of the manner in which rim chambers can be refilled.

Also, in FIG. 9, multiple chambers can be formed in the hollow rim. A refillable chamber 86 can carry an antibacterial or antiobiotic which will diffuse slowly from the chamber. A second chamber 88, refillable if desired, can carry and release a Trichomonacide and/or a Moniliacide. A Silastic panel carrying the drug, mixed while in the fluid state, can also be used. A third chamber 90 can also be used for an appropriate material to be released over a period of time. These chambers can be replenished by using a hypodermic needle, as shown in FIG. 10, to inject medication into the chambers. Small circumferentially spaced openings 92 can be used to facilitate the diffusion, but the openings are not necessary when the material used is Silastic or some similar material.

Figure 11:
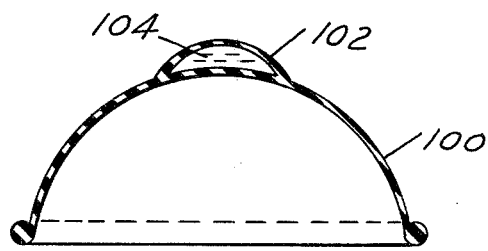
FIG. 11, a modification showing a central medicament chamber.

In FIG. 11, a diaphragm or cervical cap 100 has a pouch 102 formed at the top with breachable areas, as in FIG. 6, to effect egress of medication 104 to one or both sides of the main wall as previously described in connection with FIGS. 2 to 6.

Thus, the diaphragm or cervical cap is used not only for the customary prevention of pregnancy, but also for the prevention of such venereal diseases as gonorrhea, syphilis, Trichomonas vaginalis, moniliasis and non-specific or non-gonococcal genital infections. The described device can be used to carry the expendable matrix supported by the rim and may utilize two or more chambers for the simultaneous release of two or more anti-venereal medicaments and spermicidal compounds.

As previously indicated, applicant's invention, simultaneously to prevent VD and pregnancy (or VD alone), involves the combination of the VD prevention minimum inhibitory concentration in vivo (MIC) process and/or the automatic "prophy" (prophylaxis) process, at the time of contact, with condoms, diaphragms, cervical caps, contraceptive sponges, contraceptive and non-contraceptive liquids, jellies, creams, salves, and foams, to prevent contraction of venereal disease through the application of medicine at the proper time (during and immediately after sexual intercourse), and in the proper amount (MIC or "prophy" dosages), and in the proper location (in the human vagina).

This, in this location, the medium is applied directly to an organ of copulation and contains the preventive medication for release during intercourse in an amount and at a rate sufficient to establish and maintain a minimum inhibitory concentration dosage, or "prophy" dosage. In the described condom, the sack, cushion, or pouch can be on and preferably inside the condom and the content of the pouch will be released to give the male an automatic prophylaxis against venereal disease when the pouch ruptures during copulation or ejects a liquid stream or multiple jets or a cream, jelly, salve, or foam to contain and repel the venereal disease causing organisms that might pass into the vagina or vice versa. A pouch outside the condom will afford more protection to the female participant since it is undiluted by male semen discharge and, indeed, pouches outside and inside may be used for maximum protection to both participants.

At the present time, very costly efforts to control venereal disease are directed to education relative to awareness of the disease and substantial curative treatment. The object of the present invention is to provide preventive mediums which require no motivation relative to prevention. Birth control is an acceptable and recognized motivation which creates no embarrassment in the preparation for the act of intercourse.

With respect to the diaphragm or cervical cap, the flow may be either continuous or may be turned off or on. In addition, the cervical cap may be refilled while in situ.

The minimum inhibitory concentration dose may vary from one part of the country to another or from one country to another depending on the type and virulence of the venereal disease organism prevalent in the area. It will be appreciated also that spermicides can also be incorporated in the medication to be released to provide additional birth control protection.

It is anticipated that use of the invention by even 25% of the high risk population will result in a dramatic decrease in the incidence of gonorrhea which has at present reached almost epidemic proportions.

Thus, the present invention utilizing a condom, pouch or sack is a built-in prophylaxis station not requiring post intercourse precautions. To reiterate, the invention has the objective simultaneously to prevent venereal disease and pregnancy, or one or the other, by the application of the proper medication at the most propitious time, i.e., just before, during or immediately after intercourse, and in the proper dosages, and in the proper location, the male organ or the female vagina. The proper amount comprises the MIC, minimum inhibitory concentration in vivo, that is, the amount necessary to give the condom user and his female consort an automatic prophylaxis and to intercept the organism of NGU (non-specific genital infection such as Chlamydia) which can penetrate a condom. Thus, post intercourse precautions which present so many psychological barriers are not needed.

What is claimed as new is:

1. A method of treating and preventing venereal disease and providing birth control which comprises encapsulating a liquid venereal disease preventing medication in the distal end of a condom, providing an easily burstable wall in the encapsulation, and causing release of said medication by rupture of the burstable wall of the encapsulation during intercourse to protect the participants.

2. A birth control and venereal disease treating and prevention device comprising a mechanical birth control device, a pouch formed in the wall of said device, thin breach portions integrally formed in the wall of said pouch to rupture under pressure, and a venereal medication in said pouch to be released by the bursting of said portions during intercourse to protect the participants.

3. A device as defined in claim 2 in which said pouch is formed in the distal end of a condom, and said breach portions are formed in a septum wall separating said medication from the interior of said condom.

4. A device as defined in claim 2 in which said pouch is formed on the outside of the distal end of a condom, and said breach portions are formed in the outer wall of said pouch.

5. A device as defined in claim 2 in which a wall of said pouch is formed of a permeable material such as Silastic.

6. A method of providing birth control and treating and preventing venereal disease which comprises encapsulating a venereal disease preventing medication in a wall of a mechanical birth control device with a thin flexible wall as one wall of the encapsulation, and providing a weak burstable area in said wall to form an outlet for the medication which opens under pressure in the use of the device.

7. A birth control and venereal disease treating and prevention method as defined in claim 6 in which the medication includes Trichomonacides and Moniliacides.

8. A method as defined in claim 6 which includes forming a wall of said encapsulation of a permeable material such as Silastic.

* * * * *

UNITED STATES PATENT OFFICE
CERTIFICATE OF CORRECTION

Patent No. 4,332,243                 Dated   June 1, 1982

Inventor(s)   Morton Gutnick

It is certified that error appears in the above-identified patent and that said Letters Patent are hereby corrected as shown below:

Figure 5 should appear as shown below:

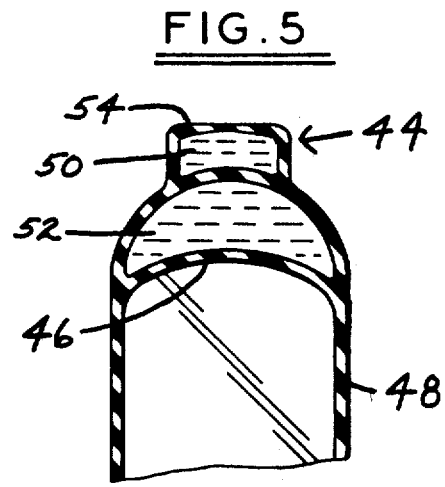

Signed and Sealed this

Twenty-first Day of September 1982

[SEAL]

Attest:

*Attesting Officer*

GERALD J. MOSSINGHOFF
*Commissioner of Patents and Trademarks*